United States Patent
Um et al.

(10) Patent No.: US 9,579,282 B2
(45) Date of Patent: Feb. 28, 2017

(54) CORE-SHELL NANOPARTICLE INCLUDING NUCLEIC ACID HYDROGEL AND METHOD OF PRODUCING THE SAME

(71) Applicant: Research & Business Foundation Sungkyunkwan University, Suwon-si (KR)

(72) Inventors: Soong Ho Um, Seoul (KR); Seung Won Shin, Seoul (KR)

(73) Assignee: RESEARCH & BUSINESS FOUNDATION SUNGKYUNKWAN UNIVERSITY, Suwon-si (KR)

( * ) Notice: Subject to any disclaimer, the term of this patent is extended or adjusted under 35 U.S.C. 154(b) by 91 days.

(21) Appl. No.: 14/515,721

(22) Filed: Oct. 16, 2014

(65) Prior Publication Data
US 2015/0283075 A1    Oct. 8, 2015

(30) Foreign Application Priority Data
Apr. 8, 2014    (KR) .................. 10-2014-0041655

(51) Int. Cl.
*C12N 9/00*    (2006.01)
*A61K 9/127*    (2006.01)

(52) U.S. Cl.
CPC ............... *A61K 9/127* (2013.01); *C12N 9/93* (2013.01)

(58) Field of Classification Search
None
See application file for complete search history.

(56) References Cited

U.S. PATENT DOCUMENTS

| | | | | |
|---|---|---|---|---|
| 5,723,147 A | * | 3/1998 | Kim .................... | A61K 9/1277 424/450 |
| 2006/0058249 A1 | * | 3/2006 | Tong .................... | A61K 9/127 514/43 |
| 2008/0241917 A1 | * | 10/2008 | Akita .................. | A61K 9/1272 435/320.1 |
| 2010/0323018 A1 | * | 12/2010 | Irvine ................. | A61K 9/0019 424/489 |
| 2010/0324124 A1 | | 12/2010 | Irvine et al. | |

FOREIGN PATENT DOCUMENTS

KR    10-2013-0054625 A    5/2013

OTHER PUBLICATIONS

Shin, Seung Won, et al. "Influence of Various Compositional Factors on the Construction of a Lipid-supported Polymeric Nanoparticulate," Presentation OP51 at The 2013 KSBB Fall Meeting and International Symposium, Oct. 17, 2013 (14 pages, in English).

Bae, Sun Ju, et al. "A gene-networked gel matrix-supported lipid bilayer as a synthetic nucleus system." Langmuir 28.49 (2012): 17036-17042.

\* cited by examiner

*Primary Examiner* — Betty Forman

(57) ABSTRACT

The present invention relates to a functional complex particle prepared by filling a nucleic acid hydrogel inside a liposome and a method of producing the same. The present invention may have an effect of increasing an expression of protein factors included in the particle by incorporating an X-shaped nucleic acid monomer in the nucleic acid hydrogel. Accordingly, when the core-shell particle is prepared using the method according to an embodiment of the present invention, an effect of facilitating an introduction of a genome into the nucleic acid hydrogel may be obtained, and thereby the core-shell particle may be used as a protein production platform copying a cell nucleus.

9 Claims, 7 Drawing Sheets

FIG. 2
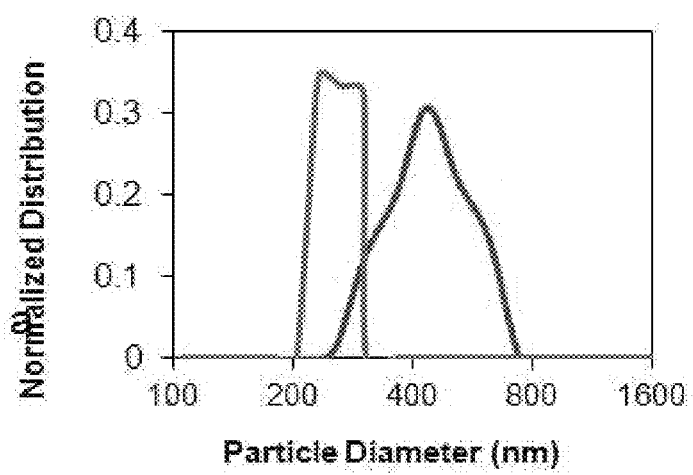
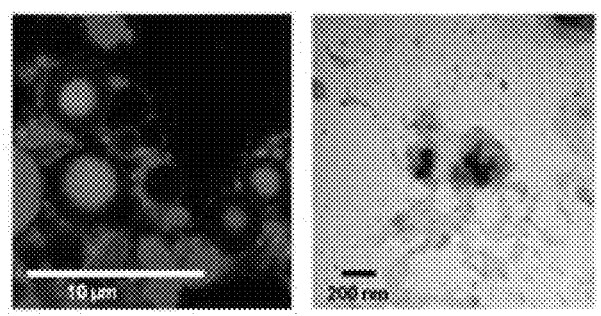

FIG. 6

```
N = 200;
d = 2.0e-6;
eta = 1.364482e-3;
kB = 1.38e-23;
T = 293;
D = kB*T/(6*pi*eta*d)

tau = 2.39;
time = tau*1:N;
k=sqrt(2*D*tau);
whilenum=1;
whilek=1;
Msd = 4*D*tau while whilenum<N;
    dx=k*randn(N,1);
    dy=k*randn(N,1);
    x = cumsum(dx);
    y = cumsum(dy);
    dSquaredDisplacement = (dx.^2) + (dy.^2);
    squareddisplacement = (x.^2) + (y.^2);

if squareddisplacement<25.0e-12
        whilek = whilenum+1;
    else whilek=whilenum;
    end;
    whilenum=whilek;

end;

simulatedD = mean(dSquaredDisplacement)/(2*3*tau)

simulatedMsd = 4*simulatedD*tau standardError=std(dSquaredDisplacement)/(2*3*tau*sqrt(N))
actualError=D-simulatedD plot(x,y);
title('Particle');

hold on;

x = -5.0e-6:1.0e-10:5.0e-6;
y = sqrt(25.0e-12-x.^2);
plot(x,y,'r','LineWidth',3);
hold off;
hold on;
plot(x,-y,'r','LineWidth',3);
hold off;
```

| Captured Time | Relative coordinate of DNA hydrogel | | Relative Displacement | Actual Displacement (m) | Square Displacement |
|---|---|---|---|---|---|
| | X coordinate | Y coordinate | | | |
| 0 | 11.23 | 10.86 | NA | NA | NA |
| 2.39 | 9.7 | 10.86 | 1.53 | 8.03E-07 | 6.45E-13 |
| 4.688 | 8.57 | 10.5 | 1.19 | 6.23E-07 | 3.88E-13 |
| 7.093 | 7.76 | 11.49 | 1.28 | 6.71E-07 | 4.51E-13 |
| 9.499 | 7.87 | 10.8 | 0.70 | 3.67E-07 | 1.35E-13 |
| 12.093 | 7.07 | 10.97 | 0.82 | 4.29E-07 | 1.84E-13 |
| 14.499 | 7.44 | 8.9 | 2.10 | 1.10E-06 | 1.22E-12 |
| 16.888 | 6.54 | 9.54 | 1.10 | 5.80E-07 | 3.36E-13 |

MSD = 4.80E-13

CORE-SHELL NANOPARTICLE INCLUDING NUCLEIC ACID HYDROGEL AND METHOD OF PRODUCING THE SAME

CROSS-REFERENCE TO RELATED APPLICATIONS

This application claims the benefit under 35 USC 119(a) of Korean Patent Application No. 10-2014-0041655 filed on Apr. 8, 2014 in the Korean Intellectual Property Office.

BACKGROUND

1. Field

The present invention relates to a core-shell nanoparticle including a genome-hydrogel and a method of producing the same.

2. Discussion of Related Art

Liposomes are spherical vesicles in which a phospholipid bilayer surrounds an aqueous phase. Constituents of lipid layers are amphipathic phospholipids composed of two hydrophobic fatty acid groups and a hydrophilic phosphate group. When exposed to an aqueous phase, the phospholipids arrange themselves into a bilayer which may form a closed structure like an artificial cell. In a bilayer structure, hydrophobic lipid tails face the inside of the layer while the hydrophilic heads face the outside thereof. Injecting a drug into the liposomes has decreased toxicity and increased pharmaceutical efficacy. Therefore, the liposomes are receiving attention as a particle structure prepared through assembly with polymers, drugs, and antigens.

However, there have been many problems with the single emulsion protocol using a bilayer of water/oil that has been used most so far in the existing process of producing single polymer particles or single lipid particles for use as a carrier in the conventional art. Especially, this conventional method only allows the use of a lipid-soluble polymer, which largely limits a range of available polymers when used for actual medical treatments. Further, clinical adaptations have exposed the limitations of unilamellar lipid particles which are easily decomposed.

Particularly, substances generated when polymers are exposed or decomposed in cells and tissues commonly damage surrounding normal cells or cause side effects such as inflammatory responses. On the other hand, water-soluble polymers are usually present naturally, and thus have an advantage of minimizing an adverse effect. Since water-soluble polymers such as polysaccharides, polydeoxyribonucleic acids, collagen, and cellulose are all present naturally and may be included into cell metabolites, side effects may be minimized upon decomposition of the water-soluble polymers.

However, when water-soluble proteins are entrapped in particles, severe side effects occur upon production and application such as aggregations of most proteins in oils. Accordingly, particles may be formed only at a predetermined concentration of the entrapped proteins. Due to a limitation of available polymers and difficulty in treating proteins, there are many difficulties in application of liposomes to living bodies such as producing immune vaccines based on protein antigens or antibodies.

Further, a nucleic acid-based hydrogel system has come into the spotlight as a new material recently. This system is being spotlighted as a new drug carrier and protein production medium, but core-shell and hydrogel systems both have severe shortcomings to apply to in vivo techniques, thereby requiring active complementary measures. In particular, strategies to maximize biocompatibility and in vivo performance through a minimization of toxicity have not yet been found.

SUMMARY

In order to address the issues on the conventional art, the present invention is directed to producing a particle by filling a nucleic acid hydrogel inside a liposome, introducing a genome into the hydrogel, and thus enabling the particle to be used as a protein production platform copying a cell nucleus.

However, the technical objectives of the present invention are not limited to the above disclosure and other objectives may become apparent to those of ordinary skill in the art based on the following descriptions.

According to an aspect of the present invention, there is provided a nucleic acid hydrogel-containing particle, in which a nucleic acid monomer is included inside a liposome formed with a lipid.

In an embodiment of the present invention, the lipid is one or more selected from the group consisting of 1-palmitoyl-2-oleoyl-sn-glycero-3-phosphocholine (POPC), 1-palmitoyl-2-oleoyl-sn-glycero-3-phospho-(1'-rac-glycerol) (POPG), 1,2-dihexadecanoyl-sn-glycero-3-phosphoethanolamine, triethylammonium salt (Texas Red DHPE), cholesterol, and mixtures thereof.

In another embodiment of the present invention, the nucleic acid hydrogel further includes a ligase.

In still another embodiment of the present invention, the ligase is selected from the group consisting of T4 ligase, thermus thermophilus ligase, mammalian DNA ligase I, mammalian DNA ligase II, and vaccinia virus DNA ligase.

In still another embodiment of the present invention, the particle further includes a genome.

In still another embodiment of the present invention, the particle is used for a production of RNAs or proteins.

Further, according to another aspect of the present invention, there is provided a method of producing the particle, including the following steps:

a) putting a lipid into an organic solvent and mixing them;

b) preparing an emulsion by adding a nucleic acid monomer and ligase to the mixed solution; and c) stacking the emulsion on an aqueous solution, and removing the organic solvent on an upper layer through centrifugation.

In an embodiment of the present invention, the lipid is one or more selected from the group consisting of 1-palmitoyl-2-oleoyl-sn-glycero-3-phosphocholine (POPC), 1-palmitoyl-2-oleoyl-sn-glycero-3-phospho-(1'-rac-glycerol) (POPG), 1,2-dihexadecanoyl-sn-glycero-3-phosphoethanolamine, triethylammonium salt (Texas Red DHPE), cholesterol, and mixtures thereof.

In another embodiment of the present invention, the organic solvent is one or more selected from the group consisting of ethylacetate, paraffin, ethylether, isopropyl acetate, n-propyl acetate, isobutyl acetate, n-butyl acetate, isobutyl isobutyrate, 2-ethylhexyl acetate, and C9 acetate.

In still another embodiment of the present invention, the aqueous solution is a glucose solution in step c).

In still another embodiment of the present invention, a genome is further mixed in step a).

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 2 is an image obtained using a transmission electron microscope and confocal microscope capable of determining a formation of particles;

FIG. 6 is a view illustrating MATLAB codes used to determine Brownian motion properties and the properties calculated therefrom.

DETAILED DESCRIPTION

Figure 1:
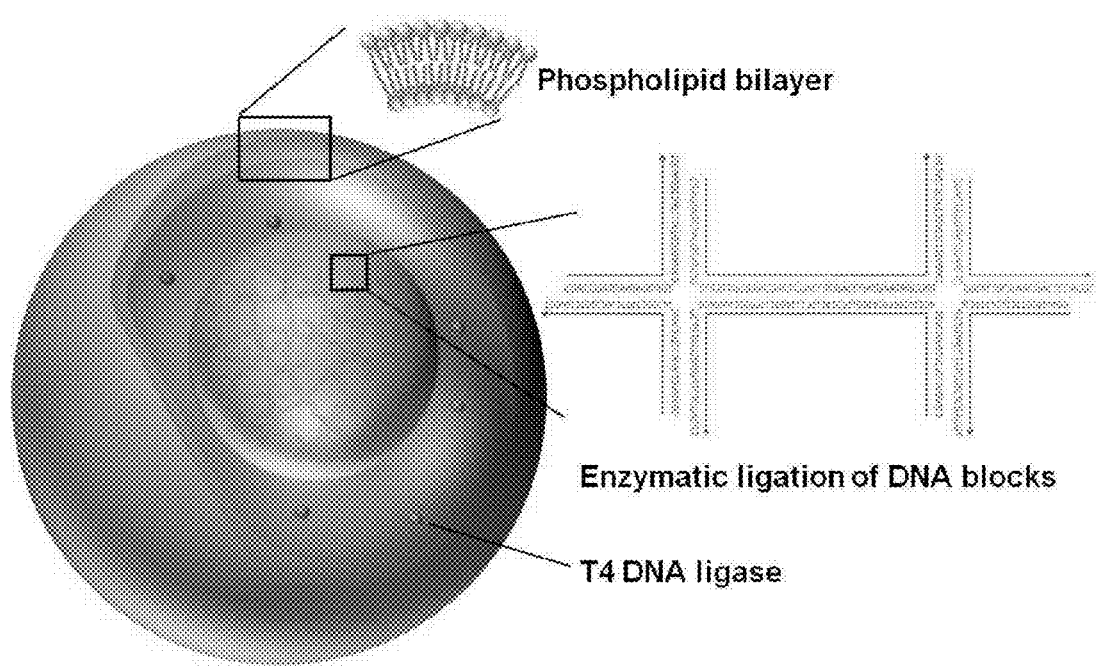
FIG. 1 is a view illustrating a structure of a core-shell nanoparticle of a nucleic acid hydrogel prepared in an embodiment of the present invention.

Based on a rapid development of the nucleic acid-based hydrogel and recognition of availability of core-shell particles, the present invention was completed as a result of a study on nanoparticles using the nucleic acid hydrogel.

In an embodiment of the present invention, a biocompatible core-lipid layer shell nanoparticle having advantages of both the core-shell particle and a nucleic acid-based hydrogel system, a maximized performance, and a new hybrid nucleic acid hydrogel introduced therein were prepared. A core-shell structure having a nucleic acid hydrogel filling inside a thin lipid layer is formed using a modified emulsion technology, the lipid layer which serves as a thin layer may be filled with polymers and various lipid-soluble or water-soluble contents, and a formation of the final particle may be systematically determined through a trapped nucleic acid and chemical reaction.

The size, surface charge, genomic gel content, or the like of the particle prepared in an embodiment of the present invention may be adjusted, and a decomposition rate of an assembly and emission rate of protein factors generated according to the decomposition rate of the assembly may be controlled depending on a target material composition according to a method of preparing an emulsion. Accordingly, the particle may be used as a multifunctional vaccine platform capable of applying to several diseases by diversifying a protein code contained in the assembly.

Therefore, the present invention is directed to providing a particle having a nucleic acid hydrogel which includes an X-shaped nucleic acid monomer and is fused inside a liposome formed with a lipid.

The particle according to an embodiment of the present invention as described above has an effect of increasing an expression of a genome contained in the particle because the X-shaped nucleic acid monomer is included. That is, by containing the X-shaped nucleic acid monomer, a nucleic acid-based hydrogel system may be provided as a new material, and this system may be used as a new drug carrier and protein production medium.

The X-shaped nucleic acid monomer is basically the same as a nucleic acid forming genes in cells, prepared to have an X-shape such that a unit has four ends, and a combination of each polydeoxyribonucleic acid is formed by a temporary crosslinking of the complementary four ends and a ligase substituting the crosslinking for a covalent bond.

In an embodiment of the present invention, the lipid may be, but is not limited to, 1-palmitoyl-2-oleoyl-sn-glycero-3-phosphocholine (POPC), 1-palmitoyl-2-oleoyl-sn-glycero-3-phospho-(1'-rac-glycerol) (POPG), 1,2-dihexadecanoyl-sn-glycero-3-phosphoethanolamine, triethylammonium salt (Texas Red DHPE), cholesterol, or mixtures thereof, and the composition and amount thereof may be segmentalized as necessary.

In another embodiment of the present invention, the nucleic acid hydrogel may further include a ligase, and the ligase may be T4 ligase, thermus thermophilus ligase, mammalian DNA ligase I, mammalian DNA ligase II, or vaccinia virus DNA ligase, and T4 ligase may be preferably used as described in an embodiment of the present invention, but the ligase is not limited thereto, and any ligase capable of joining nucleic acids may be used.

Further, in the present invention, the particle may further include a genome. The particle may be used for a production of RNAs or proteins by introducing the genome into the particle as described above.

Further, the present invention may provide a method of producing the particle including the following steps.

a) putting a lipid into an organic solvent and mixing them;

b) adding an X-shaped nucleic acid monomer and ligase to the mixed solution;

c) preparing an emulsion by stirring the solution which was added to or treating the solution which was added to with ultrasonic waves; and d) stacking the emulsion on a glucose solution, and then removing an organic solvent of an upper layer through centrifugation.

In an embodiment of the present invention, the organic solvent may be ethylacetate, paraffin, ethylether, isopropyl acetate, n-propyl acetate, isobutyl acetate, n-butyl acetate, isobutyl isobutyrate, 2-ethylhexyl acetate, ethylene glycol diacetate, C9 acetate, or mixtures thereof, but is not limited thereto.

In another embodiment of the present invention, the ultrasonic wave treatment may be performed for 0.1 to 30 seconds in step c), preferably for 5 to 15 seconds, and most preferably for 10 seconds, but is not limited thereto.

In still another embodiment of the present invention, a genome may be further mixed in step a), and thereby RNAs or proteins may be generated.

The particle prepared using the above-described method was determined to be capable of being used as a protein production platform copying a cell nucleus through examples, because the genome can be easily introduced into the nucleic acid hydrogel of the particle. The particle is determined to develop as a driving force of a single cell development in the future.

Hereinafter, the present invention will be described in detail in conjunction with the following embodiments. However, the following embodiments merely exemplify the present invention, and the present invention is not limited thereto.

EXAMPLE

Example 1

Preparation of Lipid Layer-Nucleic Acid Hydrogel Core-Shell Particle 1.1 Lipid Layer-Nucleic Acid Hydrogel Core-Shell Particle Designing In order to prepare a core-shell structure of the nucleic acid hydrogel, a design of copying a nucleic acid structure including 23 pairs of genomic material outside a lipid layer was developed. A nucleic acid structure introducing a single genome monomer was first tried, without trying a nucleic acid structure including multiple genome monomers first. A design of introducing the nucleic acid hydrogel into a core first, and then protecting it with a lipid layer was formed (refer to FIG. 1). An X-shaped nucleic acid which is a monomer of the nucleic acid hydrogel and T4 ligase were introduced inside of the lipid layer using an emulsion technology, reacted for a predetermined time, and finally a core-shell particle was designed.

1.2 Preparation and Determination of Lipid Layer-Nucleic Acid Hydrogel Core-Shell Particle Monomers of the nucleic acid hydrogel and ligase were introduced into the inside of the lipid layer using an emulsion technology.

After adding an aqueous solution which has a total volume of 0.05 ml and includes heterogeneous initial components related to the nucleic acid hydrogel (ligase:T4 DNA ligase (15 units), 10× ligase buffer (0.005 ml), a nucleic acid hydrogel X-shaped monomer (3.5 nmole), inner buffer (which is a mixed solution of 175 mM glucose and 75 mM sucrose) (0.005 ml), and SYBR green I (10000×, 0.005 ul)) to a mixed solution of a lipid and organic solvent, which was prepared by mixing 2 mg of 1-palmitoyl-2-oleoyl-sn-glycero-3-phosphocholine (POPC), 0.2 mg of 1-palmitoyl-2-oleoyl-sn-glycero-3-phospho-(1'-rac-glycerol) (POPG), 0.025 mg of 1,2-dihexadecanoyl-sn-glycero-3-phosphoethanolamine, triethylammonium salt (Texas Red DHPE), 0.4 mg of cholesterol to 0.5 ml of ethylacetate, an emulsion was formed by using an ultrasonicator (Misonic Q700) for 10 seconds.

The organic solvent included in the formed emulsion was stacked on a 250 mM glucose solution (0.4 ml), and then separated through centrifugation. A single lipid layer particle may be formed through centrifugation, due to a density difference between glucose and sucrose included in an aqueous solution inside the lipid layer and 250 mM glucose solution. In addition, a concentration of glucose and sucrose of the inner aqueous solution is the same as a mol concentration of glucose of the external aqueous solution, and thus an osmotic pressure may be minimized Thereafter, the organic solvent on an upper layer was removed, and thereby a particle into which the nucleic acid hydrogel is filled and fused was prepared.

Figure 3:
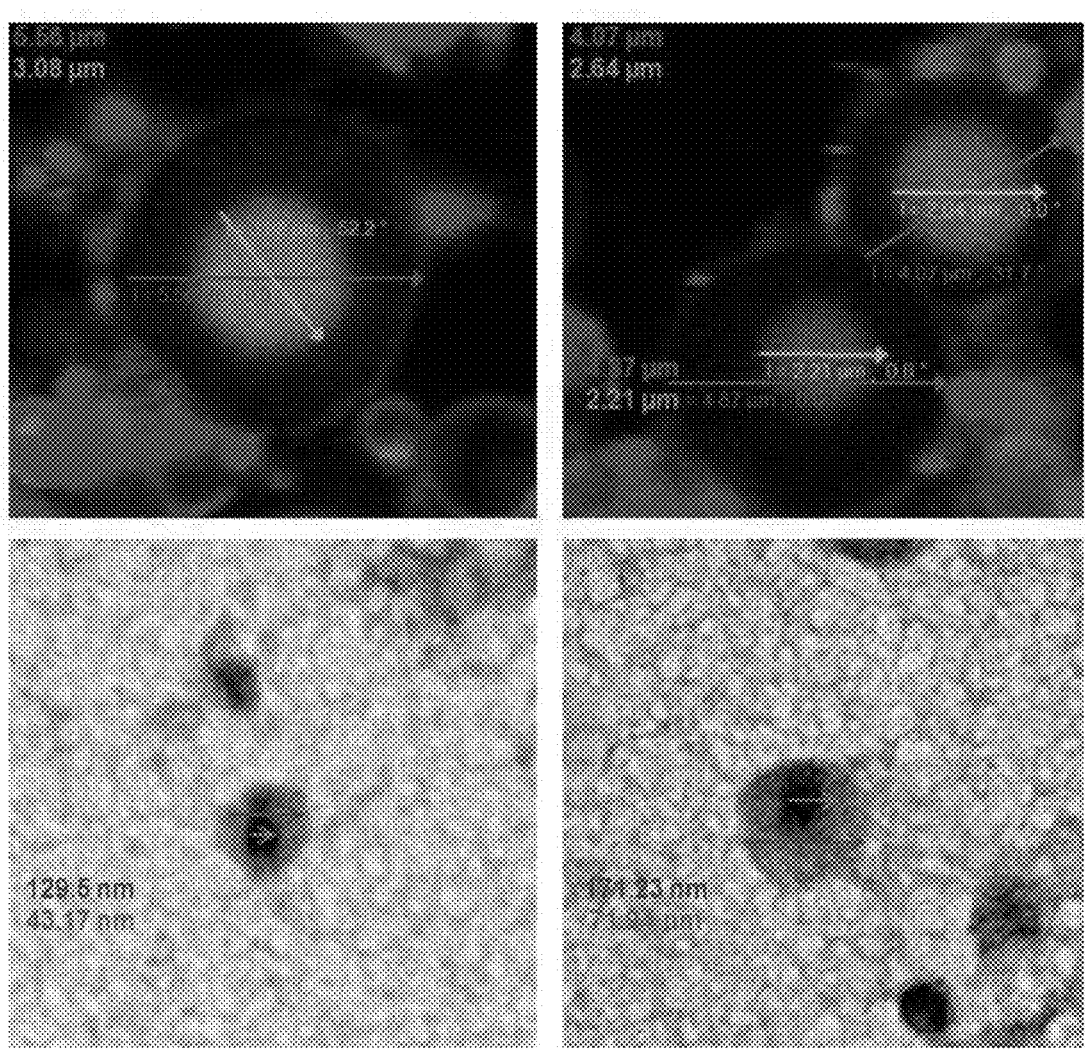
FIG. 3 is a view illustrating an evaluation result of a spatial distribution of the formed particles.

Then, the lipid layer and nucleic acid which were selectively dyed were determined using a confocal microscope or transmission electron microscope. The result was shown in FIG. 2 and FIG. 3.

1.3 Determination of Particle Formation

The synthesized particle was determined whether or not it is a nanoparticle composed of a nucleic acid hydrogel core and a lipid layer shell through various methods. First, microscope images of the particles formed according to a presence of the ligase which is essential for joining monomers in a formation of the nucleic acid gel were compared and shown in FIG. 2 and FIG. 3 (when there is no ligase, a green image representing the nucleic acid chromosome in the particle accounts for a whole body of the particle).

As a result, when the ligase works and monomers are bound to each other through an interaction, the green image was determined to account for a certain space (refer to FIG. 3) of the particle (refer to the lower left picture in FIG. 2), without accounting for a whole body of the particle. In electron microscope images (refer to the right picture in FIG. 2), a core part which is positioned at a center of the particle and entrapping the nucleic acid hydrogel was determined to be intensively stained by uranium. The sizes of the whole body of the particles and the inner nucleic acid hydrogel were measured using a nanoparticle analyzer (ELS-Z), and thereby the inner nucleic acid hydrogel were determined to account for 20.4 % of the whole space inside the lipid layer (refer to the upper picture in FIG. 2).

Example 2

Determination of Nucleic Acid Hydrogel Inside Particle

Figure 4:
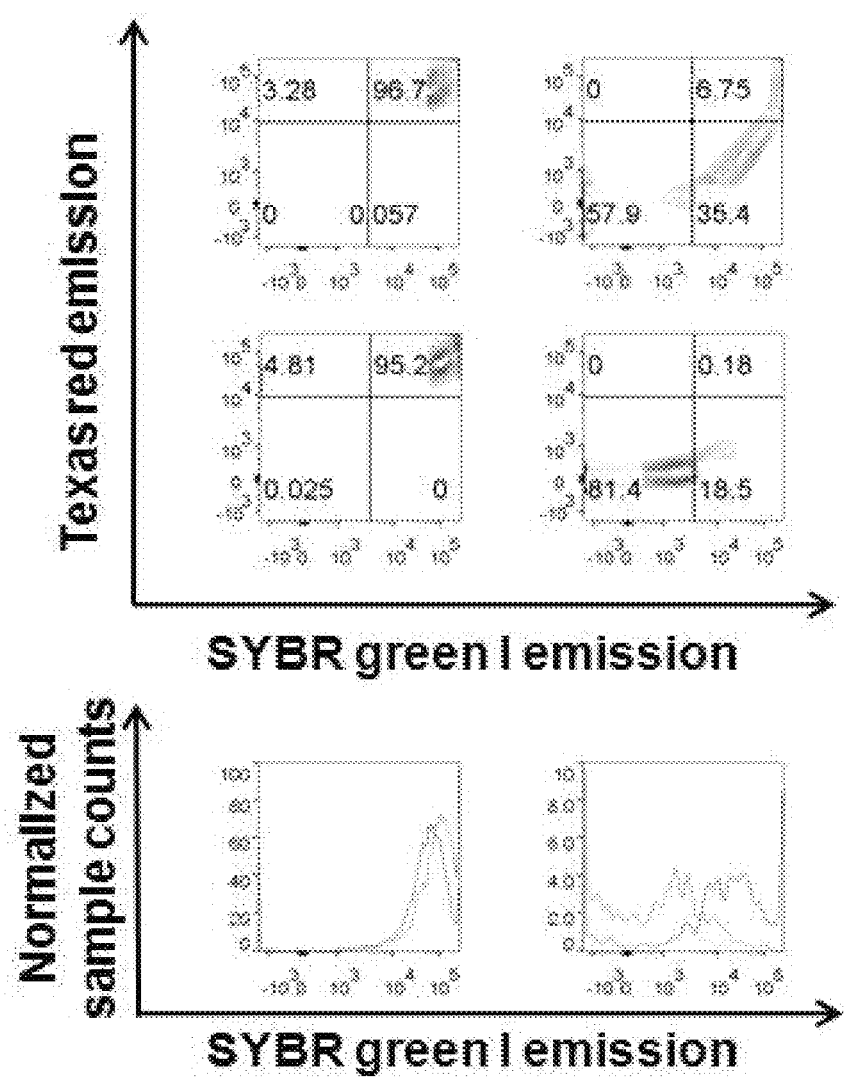
FIG. 4 is a view illustrating a result of determining whether or not the hydrogel is present in the particle using a flow cytometer.

The particle prepared in Example 1 was determined using a flow cytometer (BD FACSAria) as to whether or not the nucleic acid hydrogel is present inside the particle, and the result was shown in FIG. 4.

As shown in FIG. 4, distributions of Texas Red dye corresponding to the lipid layer and SYBR green I dye corresponding to the nucleic acid hydrogel can be all determined to increase in the particle in which the nucleic acid hydrogel was introduced (refer to FIG. 4a). Further, when the nucleic acid hydrogel is not formed, distributions of both dye corresponding to the X-shaped monomer introduced to the inside the particle and dye corresponding to the lipid layer can be also determined to increase (refer to FIG. 4b), and distributions of SYBR green I dye were determined to be the same because the structures of the particles in which the nucleic acids are introduced inside the lipid layers are the same (refer to FIG. 4c).

However, when the nucleic acid hydrogel is formed inside the particle, the hydrogel structure was maintained after removing an external lipid layer and thus an increased dye distribution can be determined to remain (refer to FIG. 4d). Relatively, when the nucleic acid hydrogel is not formed inside the particle, a smaller dye distribution can be determined after removing the external lipid layer as compared to the case in which the nucleic acid hydrogel is formed (refer to FIG. 4e). When a difference in the dye distributions is compared, the dye distribution of the nucleic acid hydrogel can be determined to be higher than that of the X-shaped structure in which the hydrogel is not formed (refer to FIG. 4f).

Example 3

Determination of Brownian Motion of Nucleic Acid Hydrogel Inside Particle

Figure 5:
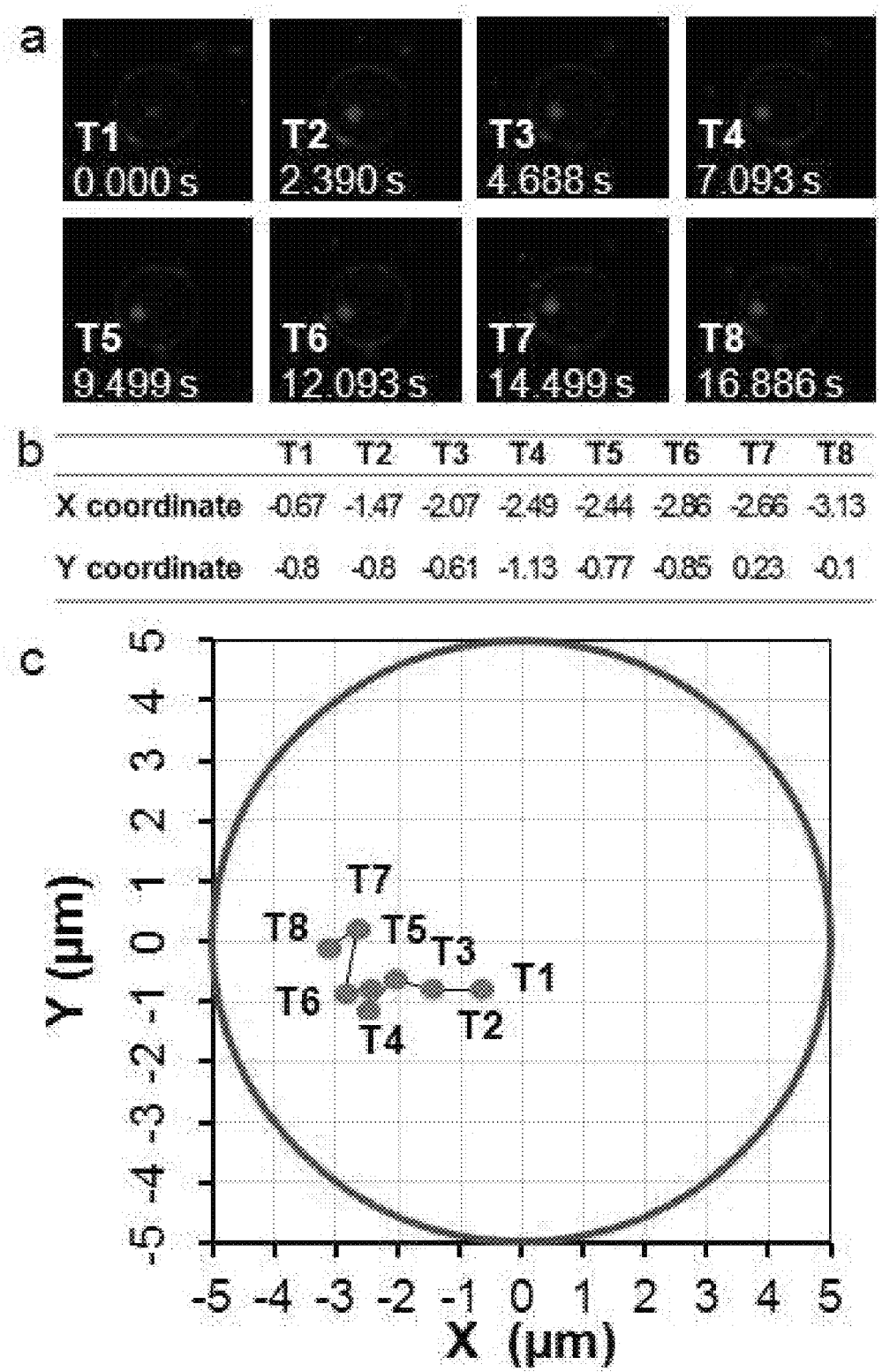
FIG. 5 is a view illustrating a result of determining mobility of the nucleic acid hydrogel.

A Brownian motion of the nucleic acid hydrogel inside the particle was determined from continuous confocal microscope (LSM 510) images as shown in FIG. 5. In FIG. 5, an irregular motion was shown in a moving path of the nucleic acid hydrogel and relative motion of the nucleic acid hydrogel inside the lipid layer (as indicated in screen coordinates). Each capture time was represented for each image (refer to FIG. 5a), and was indicated by screen coordinates (FIGS. 5b and 5c). This irregular motion was determined to be the same as the characteristics of the particle theoretically showing a Brownian motion. In FIG. 6, an MATLAB code used to determine characteristics of a theoretical Brownian motion and mean square displacement (MSD) were represented. A theoretical value was in a range of $4.107 \times 10^{-13} m^2$ to $5.117 \times 10^{-13} m^2$, and an experimental value was 4.796×

$10^{-13} m^2$, and thus the nucleic acid hydrogel can be determined to show a Brownian motion.

Example 4

Genome Introduction into Nucleic Acid Hydrogel Inside Particle

In order to apply the above-prepared new hybrid core-shell particle to a protein production, a specific genome was introduced into the nucleic acid hydrogel. A pCFE-GFP gene having a linearized form through Aat II restriction enzyme and including a green fluorescent protein (GFP) was used as a genome model, and expression factors to produce a fluorescent protein RNA were provided from a T7 High Yield RNA synthesis kit (NEB #E2040S) which is optimized to the pCFE-GFP gene and used. An X-shaped structure, 0.001 mg of the linearized pCFE-GFP gene, 0.002 ml of an inner buffer (which is a mixed solution of 175 mM glucose and 75 mM sucrose), and 10× reaction buffer, ATP (100 mM), GTP (100 mM), CTP (100 mM), UTP (100 mM), a T7 RNA polymerase mix which are presented at the T7 High Yield RNA synthesis kit were added to the organic solvent including the lipid layer compositions which are the same as the compositions used to form the nucleic acid hydrogel structure. Then, the mixed solution was treated with ultrasonic waves using an ultrasonicator (Misonic Q700) for 10 seconds to form an emulsion. Here, ethylacetate and paraffin were used as the organic solvent to form the emulsion. Thereafter, the lipid layer was formed in a same manner as that of forming the nucleic acid hydrogel structure, and the formed particle was allowed to stand at 37 degrees for 2 hours to form RNAs inside the particle.

Expressed RNAs were refined using an RNeasy mini kit (Quagen #74106) and yield of the expressed RNAs was measured using a Qubit RNA assay kit (Invitrogen #Q32852).

Figure 7:
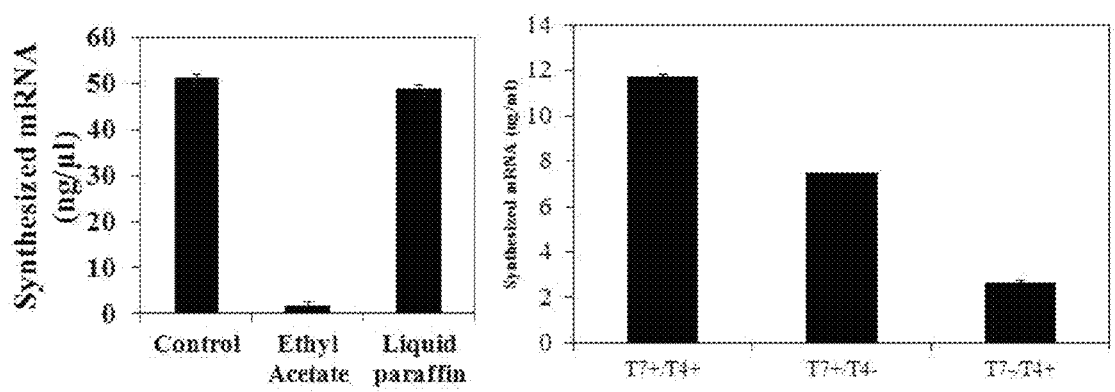
FIG. 7 is a view illustrating a result of determining whether mRNA is generated by introducing an RNA polymerase into the nucleic acid hydrogel.

When an RNA expression was activated using two different organic solvents to form the emulsion as shown in FIG. 7, the amount of RNA synthesis was determined to be similar to that of the comparative sample (control) which was naturally expressed using a liquid paraffin as the solvent. In addition, when an amount of expression was determined through a differentiation of the ligase and additional factors, the amount of RNA synthesis was determined to be high only when both T4 ligase and T7 polymerase capable of forming the nucleic acid hydrogel are included.

That is, the particle according to an embodiment of the present invention was determined to be capable of being used as an RNA and protein production platform.

The present invention has an advantage of facilitating an introduction of the genome into the nucleic acid hydrogel by designing and manufacturing the core-shell complex structure in which the single lipid layer is formed, a nucleic acid hydrogel is fused and filled through a modified single emulsion method. Accordingly, the particle according to an embodiment of the present invention can be used as a protein production platform copying a cell nucleus. In particular, the particle can be used as a driving force of a single cell development in the future.

The above-described descriptions are merely exemplifications, and it will be apparent to those skilled in the art that various modifications can be made to the above-described exemplary embodiments of the present invention without departing from the spirit or scope of the invention. Thus, it should be understood that all the embodiments described above merely exemplify the present invention in all aspects and the present invention is not limited thereto.

What is claimed is:

1. A method of producing a particle comprising a single lipid layer liposome and a nucleic acid hydrogel, the method comprising the following steps:
   a) putting a lipid into an organic solvent and mixing them;
   b) preparing an emulsion by adding a nucleic acid monomer and ligase to the mixed solution;
   c) stacking the emulsion on an aqueous solution; and
   d) centrifuging the emulsion/aqueous solution stack to thereby form the particle comprising the single lipid layer liposome and the nucleic acid hydrogel and removing the organic solvent from the particle.

2. The method of claim 1, wherein the lipid includes one or more selected from the group consisting of 1-palmitoyl-2-oleoyl-sn-glycero-3-phosphocholine (POPC), 1-palmitoyl-2-oleoyl-sn-glycero-3-phospho-(1'-rac-glycerol) (POPG), 1,2-dihexadecanoyl-sn-glycero-3-phosphoethanolamine, triethylammonium salt (Texas Red DHPE), cholesterol.

3. The method of claim 1, wherein the organic solvent includes one or more selected from the group consisting of ethylacetate, paraffin, ethylether, isopropyl acetate, n-propyl acetate, isobutyl acetate, n-butyl acetate, isobutyl isobutyrate, 2-ethylhexyl acetate, and C9 acetate.

4. The method of claim 1, wherein the aqueous solution is a glucose solution in step c).

5. The method of claim 1, wherein a genome is further mixed in step a).

6. The method of claim 1, wherein the emulsion in step b) is further prepared with an aqueous inner buffer.

7. The method of claim 6, wherein the aqueous inner buffer has a density different from the density of the aqueous solution in step c).

8. The method of claim 6, wherein a mol concentration of solutes in the aqueous inner buffer in step b) is substantially the same as a mol concentration of solutes in the aqueous solution in step c).

9. The method of claim 1, wherein the aqueous solution in step c) has a uniform density.

* * * * *